(12) United States Patent
Meier

(10) Patent No.: US 6,764,453 B2
(45) Date of Patent: Jul. 20, 2004

(54) STOMA MEASURING DEVICE

(75) Inventor: Kevin C. Meier, Affton, MO (US)

(73) Assignee: Sherwood Services AG, Schaffhausen (CH)

( * ) Notice: Subject to any disclaimer, the term of this patent is extended or adjusted under 35 U.S.C. 154(b) by 255 days.

(21) Appl. No.: 10/141,091

(22) Filed: May 8, 2002

(65) Prior Publication Data

US 2003/0212349 A1 Nov. 13, 2003

(51) Int. Cl.⁷ .............................................. A61B 5/103
(52) U.S. Cl. ...................................... 600/587; 33/512
(58) Field of Search ................................ 600/587, 593; 606/102; 33/511, 512, 701, 832, 836

(56) References Cited

U.S. PATENT DOCUMENTS

| 4,809,710 | A | | 3/1989 | Williamson |
| 4,834,712 | A | | 5/1989 | Quinn et al. ................. 604/175 |
| 4,972,845 | A | | 11/1990 | Iversen et al. |
| 5,013,318 | A | * | 5/1991 | Spranza, III ................. 33/512 |
| 5,171,248 | A | * | 12/1992 | Ellis ............................ 33/512 |
| 5,197,465 | A | * | 3/1993 | Montgomery ................ 33/512 |
| 5,248,302 | A | | 9/1993 | Patrick et al. ............... 604/178 |
| 5,343,874 | A | | 9/1994 | Picha et al. |
| 5,356,382 | A | | 10/1994 | Picha et al. ................. 604/105 |
| 5,814,098 | A | | 9/1998 | Hinnenkamp et al. ......... 623/2 |
| 6,110,200 | A | | 8/2000 | Hinnenkamp .................. 623/2 |
| 6,231,549 | B1 | | 5/2001 | Noecker et al. ............. 604/175 |
| 6,322,538 | B1 | | 11/2001 | Elbert et al. ................ 604/174 |
| 6,328,720 | B1 | | 12/2001 | McNally et al. ............ 604/332 |
| 6,494,848 | B1 | * | 12/2002 | Sommercorn et al. ....... 600/587 |

* cited by examiner

Primary Examiner—Eric F. Winakur
(74) Attorney, Agent, or Firm—Elizabeth A. O'Brien; Lawrence A. Chaletsky

(57) ABSTRACT

A device for measuring the length of a stoma is disclosed. A method to utilize the stoma measuring device is also disclosed.

11 Claims, 4 Drawing Sheets

STOMA MEASURING DEVICE

FIELD OF THE INVENTION

The present invention relates to stoma measuring devices.

BACKGROUND OF THE INVENTION

Devices to measure stoma tract lengths are well-known. Exemplary of such devices are U.S. Pat. Nos. 4,972,845; 5,356,382; and 5,343,874. One type of stoma that is measured is that which extends from the abdominal wall into the stomach. Gastrostomic feeding devices placed into this type of stoma provide nourishment to patients unable to otherwise ingest food due to the effects of a stroke, coma, serious injury or other medical problem. The preferred method for the placement of gastrostomic/enteral feeding devices is through a percutaneous endoscopic gastrostomy (PEG) which involves the non-invasive surgical creation of the stoma into the stomach through the abdominal wall using only a local anesthetic. Gastrostomic feeding devices such as enteral feeding tubes are generally used only for limited periods of time while low-profile gastrostomy devices are used in long-term or permanent installations. Gastrostomy devices generally are not adjustable, but instead are manufactured in several lengths. The length of the stoma, or the distance between the interior wall of the body cavity and the patient's outer layer of skin, varies from person to person, such as between that of an adult and a child. Therefore, when choosing the appropriate gastrostomy device it is necessary to accurately measure the stoma length.

An object of this invention is to provide an improved stoma measuring device capable of being operated with a single hand.

An additional object of this invention is to provide a method of measuring stoma length by utilizing the stoma measuring device described herein.

SUMMARY OF THE INVENTION

The present invention relates to a stoma measuring device for determining the length of a stoma. The stoma measuring device comprises an inner shaft member, an outer tubular member, and an actuation means. The inner shaft member forms the central support of the stoma measuring device. The outer tubular member is attached to the inner shaft member and to the actuation means. The outer tubular member has scale indicia on an exterior surface thereof and has an outwardly extensible distal section which defines an engaging means when extended. The actuation means causes the outer tubular member to move toward the distal end resulting in the extension of the extensible distal section of the outer tubular member. The stoma measuring device may further comprise a measuring bar surrounding the outer tubular member. The stoma measuring device is operated by depressing, preferably manually, the actuation means such that the extensible distal section extends outwardly from the inner shaft member to form engaging means by which the stoma measuring device is engaged with the inner wall of the internal body cavity. Once engaged a measurement of the stoma length is taken by reference to the scale indicia on the outer tubular member. The present invention also relates to a method of measuring stoma length by utilizing the stoma measuring device described herein.

DETAILED DESCRIPTION OF THE INVENTION

Figure 1:
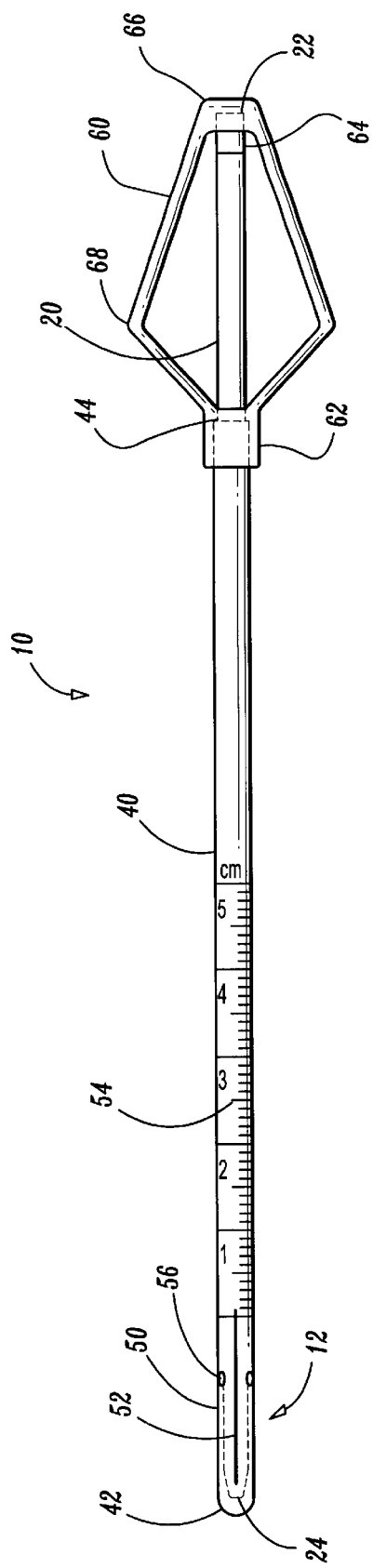
FIG. 1 is a perspective view of a stoma measuring device of the present invention.

The stoma measuring device comprises an inner shaft member, an outer tubular member, and an actuation means. The inner shaft member forms the central support of the stoma measuring device. The outer tubular member is attached to the inner shaft member and to the actuation means. The outer tubular member has scale indicia on an exterior surface thereof and has an outwardly extensible distal section which defines an engaging means when extended. The actuation means causes the outer tubular member to move toward the distal end resulting in the extension of the extensible distal section of the outer tubular member. The stoma measuring device may further comprise a measuring bar surrounding the outer tubular member. The stoma measuring device is operated by depressing, preferably manually, the actuation means such that the extensible distal section extends outwardly from the inner shaft member to form engaging means by which the stoma measuring device is engaged with the inner wall of an internal body cavity. Once engaged a measurement of the stoma length is taken by reference to the scale indicia on the outer tubular member. The present invention also relates to a method of measuring stoma length by utilizing the stoma measuring device described herein.

In more detail the inner shaft member forms the central support for the stoma measuring device. The inner shaft member is surrounded by the outer tubular member. A distal end of the inner shaft member is attached to a distal end of the outer tubular member. A proximal end of the inner shaft member is attached to a proximal end of the actuation means. Attaching the inner shaft member to both the outer tubular member and the actuation means may be accomplished in any manner such as chemical, thermal, and/or mechanical processes. Preferably, the inner shaft member is attached to the actuation means by solvent bonding. Preferably, the inner shaft member is attached to the outer tubular member by mold tipping. For purposes of this disclosure mold tipping is a process by which two members are attached, or fused together, by inserting the members into a heated mold. Attached in this manner the inner shaft member remains in a fixed position.

The inner shaft member guides the stoma measuring device through the stoma such that minimal harm to the interior of the stoma occurs. The inner shaft member may be formed from any suitable material such as commercially available polymeric and metallic materials. Exemplary polymeric materials include polypropylene, polyvinyl chloride (PVC), polyurethane, or a silicone elastomer. Preferably, the inner shaft member is comprised of a thermoplastic polyurethane.

The outer tubular member surrounds the inner shaft member with the distal end of the outer tubular member attached to the distal end of the inner shaft member. A proximal end of the outer tubular member is attached to a distal end of the actuation means. The outer tubular member comprises an outwardly extensible distal section which, when extended, provides means for engaging the stoma measuring device with the inner wall of the internal body cavity. The outwardly extensible distal section of the outer tubular member may be formed in any manner. Preferably, the outwardly extensible distal section may be formed by a plurality of short longitudinal cuts segmenting the distal end. The distal section may further comprise small holes or perforations that weaken the segments, requiring less force to outwardly extend the outwardly extensible distal section. The outer tubular member also has scale indicia on an exterior surface thereof. The scale indicia on the exterior of the outer tubular member may be comprised of any scale which may accurately indicate the length of the stoma. Preferably, the indicia are in millimeter increments.

The outer tubular member may be comprised of any flexible material, preferably a flexible polymeric material. Preferably, the outer tubular member is comprised of a thermoplastic polyurethane.

The actuation means is attached at a distal end to the outer tubular member and at a proximal end to the inner shaft member. In this manner the movement of the outer tubular member and the actuation means are interrelated. The actuation means causes the outer tubular member to move toward the distal end of the stoma measuring device. The actuation means may be characterized by a configuration such that, when operated, the outer tubular member is moved. Such a configuration of the actuation means may comprise a plurality of arms, such as a rounded, arc, or bent shape connected at a distal and a proximal end. Preferably, the actuation means comprises two oppositely facing bent arms connected at a distal and a proximal end. The actuation means may be comprised of any material that will enable movement of the outer tubular member. Exemplary of materials suitable for use as the actuation means are polypropylene, polyvinyl chloride, polyurethane, or a silicone elastomer. Preferably, the actuation means is comprised of a thermoplastic polyurethane.

The measuring bar surrounds the outer tubular member and is attached to the outer tubular member by means of a friction fit. In this manner the measuring bar is moveable along the length of the outer tubular member. The measuring bar provides a method of measuring stoma length.

The measuring bar may be comprised of any material suitable for forming a planar surface when flush with the abdominal wall. Exemplary of materials suitable for use as the measuring bar are polypropylene, polyvinyl chloride, polyurethane, or a silicone elastomer. Preferably, the measuring bar is comprised of a silicone elastomer.

Figure 2:
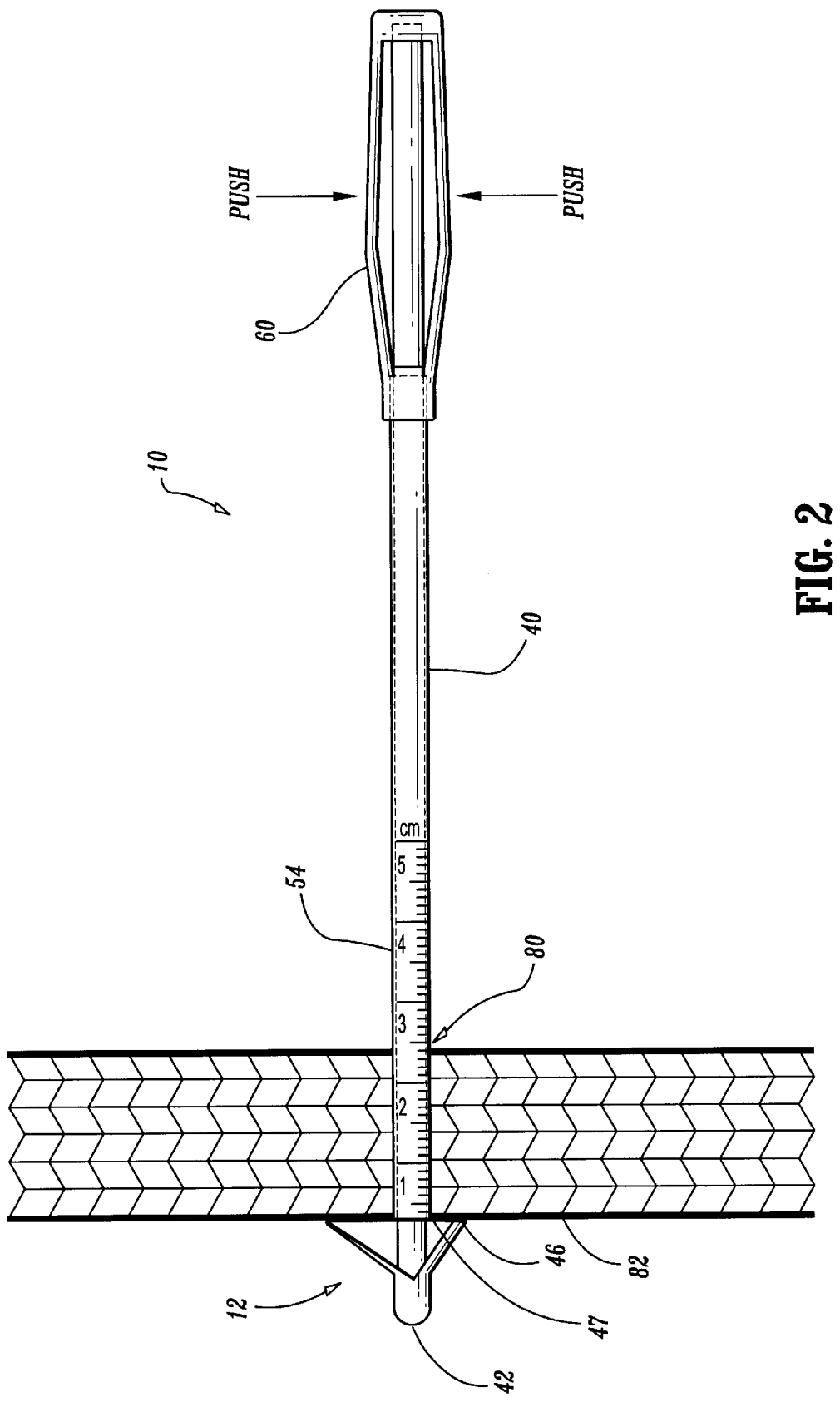
FIG. 2 is an elevational view of a stoma measuring device fully inserted into and engaged with the inner wall of the body cavity, the inner wall being shown in cross-section.

In more detail FIGS. 1 and 2 describe a stoma measuring device 10 and utilization of the stoma measuring device 10. Referring to FIG. 1, stoma measuring device 10 comprises an inner shaft member 20, an outer tubular member 40, and an actuation means 60. Inner shaft member 20 is attached to actuation means 60 at a proximal end 22 of inner shaft member 20. Outer tubular member 40 is attached to the inner shaft member 20 at distal end 42 of outer tubular member 40 and attached to actuation means 60 at proximal end 44 of outer tubular member 40. Inner shaft member 20 is comprised of thermoplastic polyurethane and is surrounded by outer tubular member 40. Distal end 42 of outer tubular member 40 is attached to distal end 24 of inner shaft member 20 by mold tipping. Actuation means 60 has a proximal end sleeve 64 into which proximal end 22 of inner shaft member 20 fits. Proximal end sleeve 64 of actuation means 60 and proximal end 22 of inner shaft member 20 are attached by solvent bonding.

The outer tubular member 40 further comprises an outwardly extensible distal section 50 which when extended provides means for engaging the stoma measuring device 10 with the inner wall of the internal body cavity. The outwardly extensible distal section 50 is formed by a plurality of short longitudinal cuts 52. The outwardly extensible distal section 50 further comprises small holes or perforations 56 that weaken the distal section 50, thereby requiring less force to cause the outwardly extensible distal section 50 to extend outwardly from the inner shaft member 20. The outer tubular member 40 further comprises scale indicia 54 on an exterior surface thereof. The zero point of the scale indicia 54 is a proximal edge 47 of engaging means 46. The scale, in millimeter increments, increases from proximal edge 47 toward the actuation means 60.

The actuation means 60 is attached at a distal end 62 to the proximal end 44 of outer tubular member 40 and at a proximal end 66 to the proximal end 22 of inner shaft member 20. In this manner the movement of the outer tubular member 40 and the actuation means 60 are interrelated. The actuation means 60 is comprised of two oppositely facing bent arms 68 connected at distal end 62 and proximal end 66 of actuation means 60. The actuation means 60 is comprised of a thermoplastic polyurethane.

Figure 3:
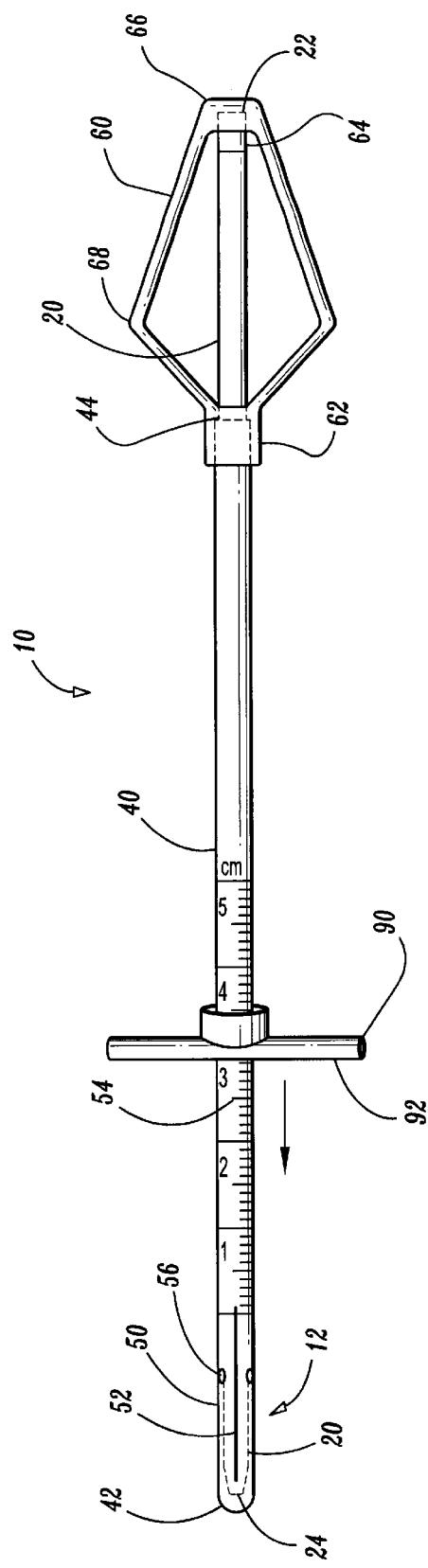
FIG. 3 is a perspective view of a preferred embodiment of the stoma measuring device of the present invention having a measuring bar.
Figure 4:
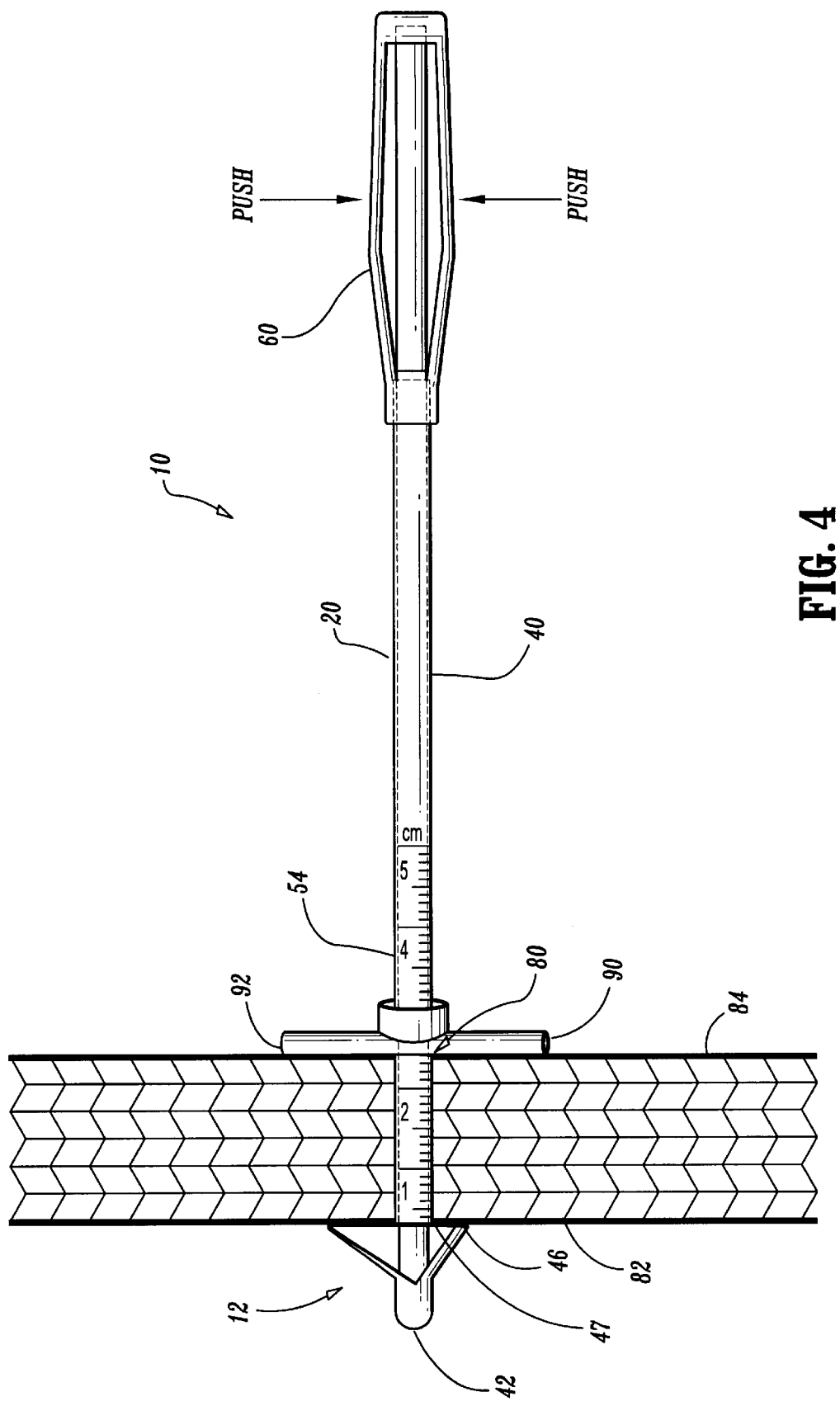
FIG. 4 is an elevational view of a preferred embodiment of the stoma measuring device of the present invention having a measuring bar.

FIG. 2 illustrates utilization of a stoma measuring device 10. The stoma measuring device 10 enables the measurement of stoma length preferably in a one hand operation. The stoma measuring device 10 is shown inserted through stoma 80. A distal end 42 of outer tubular member 40 is rounded to minimize potential tissue damage. When in operation actuation means 60 is actuated, for example by pressure, thereby causing an outer tubular member 40 to move toward a distal end 12 of stoma measuring device 10. Since the outer tubular member 40 is attached to an inner shaft member 20 at distal end 42 extension of the outer tubular member 40 at outwardly extensible distal end section 50 occurs. The stoma measuring device 10 is retracted until engaging means 46 engage interior wall 82 of an internal body cavity such as the stomach. A measurement of stoma length is then taken using scale indicia 54. Once the measurement is taken, the distal section 50 is allowed to return to the nonextended position. The stoma measuring device 10 is then removed from the stoma 80. FIGS. 3 and 4 describe a preferred embodiment of a stoma measuring device 10 and utilization of the stoma measuring device 10 wherein a measuring bar is utilized to measure stoma length. Referring to FIG. 3, stoma measuring device 10 comprises an inner shaft member 20, an outer tubular member 40, and an actuation means 60. Inner shaft member 20 is attached to actuation means 60 at a proximal end 22 of inner shaft member 20. Outer tubular member 40 is attached to the inner shaft member 20 at distal end 42 of outer tubular member 40 and attached to actuation means 60 at proximal end 44 of outer tubular member 40. Inner shaft member 20 is comprised of thermoplastic polyurethane and is surrounded by outer tubular member 40. Distal end 42 of outer tubular member 40 is attached to distal end 24 of inner shaft member 20 by mold tipping. Actuation means 60 has a proximal end sleeve 64 into which proximal end 22 of inner shaft member 20 fits. Proximal end sleeve 64 of actuation means 60 and proximal end 22 of inner shaft member 20 are attached by solvent bonding.

The outer tubular member 40 further comprises an outwardly extensible distal section 50 which when extended provides means for engaging the stoma measuring device 10 with the inner wall of the internal body cavity. The outwardly extensible distal section 50 is formed by a plurality of short longitudinal cuts 52. The outwardly extensible distal section 50 further comprises small holes or perforations 56 that weaken the distal section 50, thereby requiring less force to cause the outwardly extensible distal section 50 to extend outwardly from the inner shaft member 20. The outer tubular member 40 further comprises scale indicia 54 on an exterior surface thereof. The zero point of the scale indicia 54 is a proximal edge 47 of engaging means 46. The scale, in millimeter increments, increases from proximal edge 47 toward the actuation means 60.

The stoma measuring device 10 further comprises a measuring bar 90 surrounding outer tubular member 40. Measuring bar 90, moveable along the length of outer tubular member 40, is comprised of a silicone elastomer.

The actuation means 60 is attached at a distal end 62 to the proximal end 44 of outer tubular member 40 and at a proximal end 66 to the proximal end 22 of inner shaft member 20. In this manner the movement of the outer tubular member 40 and the actuation means 60 are interrelated. The actuation means 60 is comprised of two oppositely facing bent arms 68 connected at distal end 62 and proximal end 66 of actuation means 60. The actuation means 60 is comprised of a thermoplastic polyurethane.

FIG. 4 illustrates utilization of a preferred embodiment of a stoma measuring device 10. The stoma measuring device 10 enables the measurement of stoma length preferably in a one hand operation. The stoma measuring device 10 is shown inserted through stoma 80. A distal end 42 of outer tubular member 40 is rounded to minimize potential tissue damage. When in operation actuation means 60 is actuated, for example by pressure, thereby causing an outer tubular member 40 to move toward a distal end 12 of stoma measuring device 10. Since the outer tubular member 40 is attached to an inner shaft member 20 at distal end 42 extension of the outer tubular member 40 at outwardly extensible distal end section 50 occurs. The stoma measuring device 10 is retracted until engaging means 46 engage interior wall 82 of an internal body cavity such as the stomach. Measuring bar 90 is moved by hand along the outer tubular member 40 until it is flush with abdominal wall 84. The distal section 50 is allowed to return to the nonextended position. The stoma measuring device 10 is then removed from the stoma 80. A measurement of stoma length is then taken by referencing the scale indicia 54 at distal end 92 of measuring bar 90.

In light of the foregoing disclosure of the invention and description of the preferred embodiments, those skilled in this area of technology will readily understand that various modifications and adaptations can be made without departing from the scope and spirit of the invention. All such modifications and adaptations are intended to be covered by the following claims.

We claim:

1. A stoma measuring device comprising:
   a. an inner shaft member having a distal end attached to an outer tubular member and a proximal end attached to an actuation means;
   b. said outer tubular member attached to said actuation means at a proximal end of said outer tubular member and attached to said inner shaft member at a distal end of said outer tubular member, said outer tubular member having scale indicia on an exterior surface thereof and having an outwardly extensible distal section which provides means for engaging the inner wall of an internal body cavity with the stoma measuring device;
   c. said actuation means attached to said proximal end of said outer tubular member capable of causing said outer tubular member to move toward the distal end of the stoma measuring device such that the extensible distal section outwardly extends to create said engaging means.

2. The stoma measuring device according to claim 1 wherein said actuation means comprises at least two arms connected at a distal end and a proximal end of said actuation means.

3. The stoma measuring device according to claim 2 wherein said actuation means comprises at least two oppositely facing bent arms connected at a distal end and a proximal end of said actuation means.

4. The stoma measuring device according to claim 1 wherein said outwardly extensible distal section comprises short longitudinal cuts.

5. The stoma measuring device according to claim 4 wherein said outwardly extensible distal section further comprises perforations.

6. The stoma measuring device according to claim 1 further comprising a measuring bar attached to said outer tubular member.

7. The stoma measuring device according to claim 1 wherein the internal body cavity is the stomach.

8. A method of measuring stoma length comprising:
   a. inserting the stoma measuring device of claim 1 into a stoma;
   b. actuating said actuation means to cause said outer tubular member to move toward the distal end of the stoma measuring device;
   c. retracting the stoma measuring device until said engaging means engage the inner wall of the internal body cavity; and
   d. measuring the stoma using said scale indicia.

9. A stoma measuring device comprising:
   a. an inner shaft member having a distal end attached to an outer tubular member and a proximal end attached to an actuation means;
   b. said outer tubular member attached to said actuation means at a proximal end of said outer tubular member and attached to said inner shaft member at a distal end of said outer tubular member, said outer tubular member having scale indicia on an exterior surface thereof and having an outwardly extensible distal section which provides means for engaging the inner wall of an internal body cavity with the stoma measuring device, said outwardly extensible distal section having short longitudinal cuts;
   c. said actuation means comprising two oppositely facing bent arms attached to said proximal end of said outer tubular member capable of causing said outer tubular member to move toward the distal end of the stoma measuring device such that the extensible distal section outwardly extends to create said engaging means; and
   d. a measuring bar secured to said outer tubular member.

10. The stoma measuring device according to claim 9 wherein the internal body cavity is the stomach.

11. A method of measuring stoma length comprising:
    a. inserting the stoma measuring device of claim 9 into a stoma;
    b. actuating said actuation means to cause said outer tubular member to move toward the distal end of the stoma measuring device;
    c. retracting the stoma measuring device until said engaging means engage the inner wall of the internal body cavity;
    d. moving said measuring bar along said outer tubular member until said measuring bar is flush with the abdominal wall; and
    e. measuring the stoma length by reference to said scale indicia on said measuring bar.

* * * * *